United States Patent
Hagiya

(10) Patent No.: US 7,276,622 B2
(45) Date of Patent: Oct. 2, 2007

(54) METHOD FOR PRODUCING OXYGEN-CONTAINING COMPOUND

(75) Inventor: Koji Hagiya, Ibaraki (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 199 days.

(21) Appl. No.: 10/548,571

(22) PCT Filed: Mar. 23, 2004

(86) PCT No.: PCT/JP2004/003967

§ 371 (c)(1),
(2), (4) Date: Sep. 12, 2005

(87) PCT Pub. No.: WO2004/085376

PCT Pub. Date: Oct. 7, 2004

(65) Prior Publication Data

US 2006/0173221 A1 Aug. 3, 2006

(30) Foreign Application Priority Data

Mar. 26, 2003 (JP) .............................. 2003-085681

(51) Int. Cl.
*C07C 69/74* (2006.01)
*C07C 61/04* (2006.01)
*C07C 45/00* (2006.01)
*C07C 27/00* (2006.01)
*C01B 19/04* (2006.01)

(52) U.S. Cl. ...................... 560/124; 562/506; 568/449; 568/910; 423/509

(58) Field of Classification Search .................... None
See application file for complete search history.

(56) References Cited

FOREIGN PATENT DOCUMENTS

JP 34-2426 B1 4/1959

OTHER PUBLICATIONS

Kim et al, Angewandte Chemie, International Edition, Ionic Liquids Containing Anionic Selenium Species: Applications for the Oxidative Carbonylation of Aniline, 2002, 41(22) pp. 4300-4303.*
Umbreit, M.A. et al., Journal of the American Chemical Society, 1977, vol. 99, No. 16, pp. 5526 to 5528.
Mehta, G. et al., Tetrahedron Letters, 2002, vol. 43, pp. 6975 to 6978.
Otera et al., J. Org. Chem., vol. 51, pp. 3834-3838, (1986).
Marshall et al., J. Org. Chem., vol. 53, pp. 4108-4112, (1988).

* cited by examiner

*Primary Examiner*—Paul A. Zucker
(74) *Attorney, Agent, or Firm*—Birch, Stewart, Kolasch & Birch, LLP

(57) ABSTRACT

It is provided that a method for producing an oxygen-containing compound, characterized in that an olefin compound having a carbon-carbon double bond which is bonded to a methyl or methylene group is reacted with an organic hydroperoxide in the presence of an ionic liquid and a selenium compound.

12 Claims, No Drawings

METHOD FOR PRODUCING OXYGEN-CONTAINING COMPOUND

TECHNICAL FIELD

The present invention relates to a method for producing an oxygen-containing compound.

BACKGROUND ART

An oxygen-containing compound such as an alcohol compound, a ketone compound, an aldehyde compound and a carboxylic acid compound obtained by oxidizing a methyl or methylene group of an olefin compound having carbon-carbon double bond which is bonded to the methyl or methylene group such as a 1-propenyl, 2-propenyl and 2-methyl-1-propenyl group (hereinafter simply referred to as the olefin compound), is very important compound as various chemicals and synthetic intermediate of them. For example, 3,3-dimethyl-2-E-(2-carboxy-1-propenyl)cyclopropanecarboxylic acid esters obtained by oxidizing a methyl group of 2-methyl-1-propenyl group of 3,3-dimethyl-2-(2-methyl-1-propenyl)cyclopropanecarboxylic acid esters is an important chrysanthemic acid derivative as an acid part of household agents for epidemic prevention and insecticides which is known as pyrethrates (e.g. Synthetic Pyrethroid Insecticides: Structure and Properties, 3 (1990)). E,E-2,6-dimethyl-2,6-octadiene-1,8-diol-8-acetate, which is obtained by oxidizing a terminal methyl group of geranyl acetate, is useful as an intermediate in natural-product synthesis (e.g. Tetrahedron Letters, 42, 2205 (2001)).

A methyl or methylene group which is bonded to a carbon-carbon double bond of an olefin compound is the methyl or methylene group at allylic position. As a method for producing an oxygen-containing compound by oxidizing the methyl or methylene group at allylic position, for example, method for reacting the above-mentioned olefin compound with selenium dioxide (e.g. Comprehensive Organic Synthesis, 7, 83 (1991) and Proc. Japan Acad., 32, 353 (1956)) and method for reacting an olefin compound with an organic hydroperoxide in the presence of selenium dioxide catalyst (e.g. J. Amer. Chem. Soc., 99, 5526 (1977)) are known. However, in the former method, a large amount of selenium dioxide is used and it is necessary to oxidize the selenium metal again for reuse since they are converted to selenium metal after completion of the reaction. In the latter method, methylene chloride, which has some problems on the occupational safety and health, is used as a solvent and it is difficult to recover and reuse of selenium dioxide catalyst. Neither method was satisfactory industrially.

DISCLOSURE OF THE INVENTION

According to the present invention, an oxygen-containing compound such as a corresponding alcohol compound, a corresponding aldehyde compound, a corresponding ketone compound, and a corresponding carboxylic acid compound can be obtained by reacting the above-mentioned olefin compound with an organic hydroperoxide using an ionic liquid and a selenium compound to oxidize the methyl or methylene group at allylic position. It is also easy to recover and reuse the ionic liquid and selenium compound. It is industrially advantageous.

That is, the present invention provides a method for producing an oxygen-containing compound, characterized in that an olefin compound having carbon-carbon double bond which is bonded to a methyl or methylene group is reacted with an organic hydroperoxide in the presence of an ionic liquid and a selenium compound.

BEST MODE FOR CARRYING OUT THE INVENTION

An olefin compound in the present invention is not particularly limited in so far as it is an olefin compound having a structure bonding a methyl or methylene group to a carbon-carbon double bond, such as a 1-propenyl, 2-propenyl and 2-methyl-1-propenyl group, within the molecule and examples thereof include a compound of formula (1)

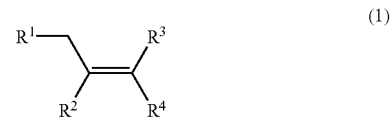

wherein $R^1$ represents a substituted or unsubstituted alkyl group, a substituted or unsubstituted aryl group, or a substituted or unsubstituted aralkyl group; $R^2$, $R^3$ and $R^4$ are the same or different, and independently represent a substituted or unsubstituted alkyl group, a substituted or unsubstituted alkoxy group, a substituted or unsubstituted aryl group, a substituted or unsubstituted aryloxy group, a substituted or unsubstituted aralkyl group, a substituted or unsubstituted aralkyloxy group, a substituted or unsubstituted alkylcarbonyl group, a substituted or unsubstituted arylcarbonyl group, a substituted or unsubstituted aralkylcarbonyl group, a substituted or unsubstituted alkoxycarbonyl group, a substituted or unsubstituted aryloxycarbonyl group, a substituted or unsubstituted aralkyloxycarbonyl group, a halogen atom or a hydrogen atom, and herein, at least one pair selected from $R^1$ and $R^3$, $R^2$ and $R^4$, $R^1$ and $R^2$, and $R^3$ and $R^4$ may be combined together with the carbon atom to which they are bonded to form a ring (hereinafter, simply referred to as the compound (1)), and a compound of formula (4)

wherein $R^2$, $R^3$ and $R^4$ are as defined above, and herein, $R^2$ and $R^4$ or $R^3$ and $R^4$ may be bonded together with the carbon atom to which they are bonded to form a ring (hereinafter, simply referred to as the compound (4)).

In the compound represented by the formula (1), and the corresponding compound represented by the formula (2) and (3), the compound wherein $R^2$, $R^3$ and $R^4$ are the same or different, and independently represent a substituted or unsubstituted alkoxy group, a substituted or unsubstituted aryl group, a substituted or unsubstituted aryloxy group, a substituted or unsubstituted aralkyloxy group, a substituted or unsubstituted alkylcarbonyl group, a substituted or unsubstituted arylcarbonyl group, a substituted or unsubstituted aralkylcarbonyl group, a substituted or unsubstituted alkoxycarbonyl group, a substituted or unsubstituted aryloxycarbonyl group, a substituted or unsubstituted aralkyloxycarbonyl group, a carboxyl group, a halogen atom or a hydrogen atom is exemplified. Further, in the compound represented by the formula (1), and the corresponding compound represented by the formula (2) and (3), the compound wherein $R^2$, $R^3$ and $R^4$ are the same or different, and independently represent a substituted or unsubstituted aryl group, a substituted or unsubstituted alkylcarbonyl group, a substituted or unsubstituted arylcarbonyl group, a substituted or unsubstituted aralkylcarbonyl group, a substituted or unsubstituted alkoxycarbonyl group, a substituted or unsubstituted aryloxycarbonyl group, a substituted or unsubstituted aralkyloxycarbonyl group, a carboxyl group, a halogen atom or a hydrogen atom is exemplified.

Examples of the unsubstituted aryl group in the unsubstituted aryl group, the unsubsutituted aryloxy group, and the unsubstituted aryloxycarbonyl group represented by $R^1$ to $R^4$ include, for example, an unsubsutituted phenyl group and an unsubstituted naphthyl group.

Examples of the unsubstituted alkyl group in the unsubstituted alkyl group, the unsubstituted alkoxy group and unsubstituted alkoxycarbonyl group include, for example, linear, blanched or cyclic alkyl groups having 1 to 20 carbon atoms such as a methyl, ethyl, n-propyl, isopropyl, n-butyl, isobutyl, sec-butyl, tert-butyl, n-pentyl, hexyl, heptyl, octyl, nonyl, n-decyl, cyclopropyl, 2,2-dimethylcyclopropyl, cyclopentyl, cyclohexyl, menthyl, undecyl, dodecyl, tridecyl, tetradecyl, pentadecyl, hexadecyl, heptadecyl, octadecyl, nonadecyl, and dodecyl group.

Examples of the substituted alkyl group include the alkyl group substituted with a substituted or unsubstituted alkoxy group, a substituted or unsubstituted aryloxy group, a substituted or unsubstituted aralkyloxy group, a halogen atom, a substituted or unsubstituted alkylcarbonyl group, a substituted or unsubstituted arylcarbonyl group, a substituted or unsubstituted aralkylcarbonyl group, a substituted or unsubstituted alkoxycarbonyl group, a substituted or unsubstituted aryloxycarbonyl group, a substituted or unsubstituted aralkyloxycarbonyl group, carboxyl group and the like, which are described hereinafter. Examples of thus substituted alkyl group include specifically, for example, a chloromethyl, fluoromethyl, trifluoromethyl, methoxymethyl, ethoxymethyl, methoxyethyl, methoxycarbonylmethyl group.

Examples of the substituted or unsubstituted alkoxy group include, for example, those which are composed of the above-mentioned substituted or unsubstituted alkyl groups and oxygen atoms. A part of the specific examples thereof include, for example, a methoxy, ethoxy, n-propoxy, isopropoxy, n-butoxy, isobutoxy, sec-butoxy, tert-butoxy, n-pentyloxy, n-decyloxy, cyclopentyloxy, cyclohexyloxy, menthyloxy, chloromethoxy, fluoromethoxy, trifluoromethoxy, methoxymethoxy, ethoxymethoxy and methoxyethoxy group.

Examples of the substituted aryl group (for example, a phenyl group and a naphthyl group) include aryl groups substituted with a substituent such as the above-mentioned substituted or unsubstituted alkyl group, the above-mentioned substituted or unsubstituted alkoxy group, the above-mentioned aryl group, a substituted or unsubstituted aralkyl group described hereinafter, a substituted or unsubstituted aryloxy group described hereinafter, a substituted or unsubstituted aralkyloxy group described hereinafter, and a halogen atom described hereinafter.

Examples of thus substituted aryl group include, for example, a 2-methylphenyl, 4-chlorophenyl, 4-methylphenyl, 4-methoxyphenyl and 3-phenoxyphenyl group. Examples of the substituted or unsubstituted aryloxy group include, for example, those which are composed of the above-mentioned substituted or unsubstituted aryl groups and oxygen atoms, such as a phenoxy, 2-methylphenoxy, 4-chlorophenoxy, 4-methylphenoxy, 4-methoxyphenoxy and 3-phenoxyphenoxy group.

Examples of the substituted or unsubstituted aralkyl group include, for example, those which are composed of the above-mentioned substituted or unsubstituted aryl groups and the above-mentioned alkyl groups, such as a benzyl, 4-chlorobenzyl, 4-methylbenzyl, 4-methoxylbenzyl, 3-phenoxybenzyl, 2,3,5,6-tetrafluorobenzyl, 2,3,5,6-tetrafluoro-4-methylbenzyl, 2,3,5,6-tetrafluoro-4-methoxybenzyl, and 2,3,5,6-tetrafluoro-4-methoxymethylbenzyl group.

Examples of the substituted or unsubstituted aralkyloxy group include, for example, those which are composed of the above-mentioned substituted or unsubstituted aralkyl groups and oxygen atoms, such as a benzyloxy, 4-chlorobenzyloxy, 4-methylbenzyloxy, 4-methoxylbenzyloxy, 3-phenoxybenzyloxy, 2,3,5,6-tetrafluorobenzyloxy, 2,3,5,6-tetrafluoro-4-methylbenzyloxy, 2,3,5,6-tetrafluoro-4-methoxybenzyloxy and 2,3,5,6-tetrafluoro-4-methoxymethylbenzyloxy group.

Examples of the halogen atom include, for example, a fluorine, chlorine and bromine atom.

Examples of the substituted or unsubstituted alkylcarbonyl group, the substituted or unsubstituted arylcarbonyl and aralkylcarbonyl group include, for example, those which are composed of carbonyl groups and the above-mentioned substituted or unsubstituted alkyl, aryl or aralkyl groups, such as an acetyl, ethylcarbonyl, benzoyl and benzylcarbonyl group.

Examples of the substituted or unsubstituted alkoxycarbonyl, aryloxycarbonyl and aralkyloxycarbonyl group include, for example, those which are composed of carbonyl groups and the above-mentioned substituted or unsubstituted alkoxy, aryloxy or aralkyloxy groups. Specific examples thereof include, for example, a methoxycarbonyl, ethoxycarbonyl, phenoxycarbonyl and benzyloxycarbonyl group. Examples of the ring formed by combining at least one pair selected from a pair of $R^1$ and $R^3$, $R^2$ and $R^4$, $R^1$ and $R^2$, and $R^3$ and $R^4$ together with the carbon atom to which they are bonded include optionally substituted cycloalkenyl rings having 5 to 8 carbon atoms, which is composed of the above-mentioned substituted or unsubstituted alkyl group and the double bond moiety.

Examples of the olefin compound include, for example, geranyl acetate, geranyl benzoate, geranyl methyl ether, geranyl benzyl ether, geranyl phenyl sulfone, geranylacetone, prenyl acetate, 7-octenoic acid methyl ester, 1-hexene, 1-heptene, 1-octene, 1-dodecene, cyclopentene, cyclohexene, cycloheptene, cyclooctene, 3-methylcyclopentene, 4-methylcyclopentene, 3,4-dimethylcyclopentene, 3-chlorocyclopentene, 1-methylcyclohexene, 1,4-dimethylcyclohexene, 3-methylcyclohexene, 2-hexene, 1,7-octadiene, 1,2,3,4-tetrahydrophthalic anhydride, indene, α-methylstyrene, β-methylstyrene, β-benzylstyrene, 4-methoxy-6-methyl-2H-pyran-2-one, methylenecyclobutane, methylenecyclopentane, β-pinene, α-methylene-γ-butyrolactone, cyclohexylidenecyclohexane, pulegone, isophorone, 2-carene, 3-carene, and α-pinene.

The present reaction is that the olefin compound is reacted with an organic hydroperoxide in the presence of an ionic liquid and a selenium compound to obtain an oxygen-containing compound obtained by oxidizing a methyl or methylene group bonded to the carbon-carbon double bond of the olefin compound. When the olefin compound having a structure bonding a methyl group to the carbon-carbon double bond is used, at least one compound selected from an alcohol compound, an aldehyde compound and a carboxylic acid compound is obtained. The producing ratio thereof differs depending on the amount of the organic hydroperoxide used and/or reaction condition. Alternatively, when the olefin compound having a structure bonding a methylene group to the carbon-carbon double bond is used, an alcohol compound, an aldehyde compound or a mixture thereof is obtained. The producing ratio thereof differs depending on the amount of the organic hydroperoxide used and/or reaction condition.

When the above-mentioned compound (1), for example, is used as the olefin compound, a compound of formula (2)

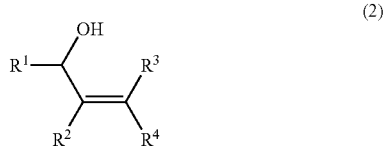

(2)

wherein $R^1$, $R^2$, $R^3$ and $R^4$ are as defined above, a compound of formula (3)

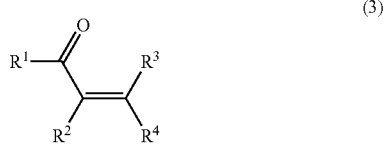

(3)

wherein $R^1$, $R^2$, $R^3$ and $R^4$ are as defined above, or a mixture thereof is obtained. Further, it will be illustrated by the specifically compounds below. When cyclohexene is used as the olefin compound, 2-cyclohexenol and 2-cyclohexenone are obtained. When the compound (4), for example, is used as the olefin compound, at least one compound selected from a compound of formula (5)

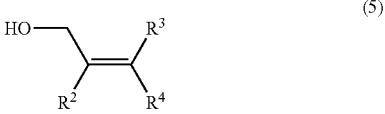

(5)

wherein $R^2$, $R^3$ and $R^4$ are as defined above, a compound of formula (6)

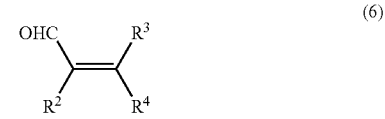

(6)

wherein $R^2$, $R^3$ and $R^4$ are as defined above, and a compound of formula (7)

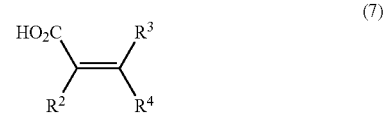

(7)

wherein $R^2$, $R^3$ and $R^4$ are as defined above. Typically, the compounds represented by the formula (5), (6) and (7), the compounds represented by the formula (5) and (6), or the compounds represented by the formula (6) and (7) depending on the amount of the organic hydroperoxide and/or the reaction condition. Furthermore, it will be illustrated by the specifically compound below. When isophorone is used as the olefin compound, three compounds described below, 3-hydroxymethyl-5,5-dimethyl-2-cyclohexen-1-one, formylisophorone and 5,5-dimethyl-3-oxo-1-cyclohexenen-1-carboxylic acid, are obtained and the former exemplified compound or the latter two compounds among three compounds were obtained depending on the reaction condition. The obtained compounds were separated, if necessary, by the method such as extraction, column chromatography and distillation as following.

Examples of the selenium compound include, for example, a divalent, tetravalent or hexavalent selenium compound such as selenium dioxide, selenium disulfide, seleninyl chloride, selenic acid, selenious acid, selenium tetrachloride, selenocystine, selenourea and dimethylselenourea, preferably selenium dioxide, selenic acid and selenious acid. The selenium compound is used alone or in the form of a mixture. The amount used of the selenium compound is usually 0.001 to 0.95 mole per 1 mol of the olefin compound.

Examples of the organic hydroperoxide include, for example, tert-butylhydroperoxide, tert-amylhydroperoxide, cumenehydroperoxide, and cymenehydroperoxide. The organic hydroperioxide is usually used in a form of an aqueous solution or an organic solvent solution. A concentration of an organic hydroperoxide in the aqueous solution or the organic solvent solution is not particularly limited, and taking into consideration volume efficiency and safety, it is about 1 to 90% by weight practically.

In the present invention, the amount of the organic hydroperoxide may be selected suitably according to the desired oxygen-containing compound since the kind and the producing ratio of the obtained compounds differs depending on the amount of the organic hydroperoxide. In the case of the alcohol compound is an objective compound, the amount used of the organic hydroperoxide is usually about 1 to 2 moles per 1 mole of the olefin compound. In the case of the aldehyde compound is an objective compound, the amount used of the organic hydroperoxide is usually about 2 to 3 moles per 1 mole of the olefin compound. In the case of the ketone compound is an objective compound, the amount used of the organic hydroperoxide is usually 2 moles or more and there is no specific upper limit and it is 50 moles or less practically taking into consideration economical viewpoint. In the case of the carboxylic acid compound is an objective compound, the amount of the organic hydroperoxide used is usually 3 moles or more and there is no specific upper limit and it is 50 moles or less practically taking into consideration economical viewpoint.

The ionic liquid include a compound comprising an organic cationic species and an anionic species, which has a melting point of 100° C. or less and is stable to hold liquid state until high temperature of about 300° C., and it is also called as Room Temperature Molten Salt. Examples of the ionic liquid include an imidazolium salt substituted with one or more alkyl groups, a pyridinium salt substituted with one or more alkyl groups, a quaternary ammonium salt, a quaternary phosphonium salt and tertiary sulfonium salt, which has a melting point of 100° C. or less and is stable to hold liquid state until high temperature of about 300° C., preferably an imidazolium salt substituted with one or more alkyl groups, which has a melting point of 100° C. or less and is stable to hold liquid state until high temperature of about 300° C.

Examples of the imidazolium salt substituted with one or more alkyl groups include salts which are composed of an imidazolium cation, of which at least one nitrogen atom on the imidazoline ring is bonded to a substituted or unsubstituted alkyl group, and anionic species such as a tetrafluoroborate, chloride, bromide, iodide, hexafluorophosphate, bis (perfluoroalkanesulfonyl) amide, alkylcarboxylate and alkanesulfonate anion. Herein, examples of the substituted or unsubstituted alkyl group include, for example, lower alkyl group having 1 to 8 carbon atoms such as a methyl, ethyl, n-propyl, isopropyl, n-butyl, isobutyl, n-pentyl, hexyl, heptyl and octyl group, and those substituted with an alkoxy group having 1 to 8 carbon atoms such as a methoxy, ethoxy, propoxy, butoxy, pentyloxy, hexyloxy, heptyloxy and octyloxy group, at least one halogen atom such as a fluorine, chlorine and bromine atom, or the like, such as a chloromethyl, fluoromethyl, trifluoromethyl, methoxymethyl, ethoxymethyl, methoxyethyl and methoxycarbonylmethyl group. Thus substituted or unsubstituted alkyl group may be also bonded to a carbon atom on the imidazoline ring.

Examples of the imidazolium salt substituted with one or more alkyl groups include, for example, an imidazolium tetrafluoroborate substituted with one or more alkyl groups such as 1-methyl-3-methylimidazolium tetrafluoroborate, 1-methyl-3-ethylimidazolium tetrafluoroborate, 1-methyl-3-butylimidazolium tetrafluoroborate, 1-methyl-3-isobutylimidazolium tetrafluoroborate, 1-methyl-3-methoxyethylimidazolium tetrafluoroborate, 1-ethyl-3-ethylimidazolium tetrafluoroborate, 1-ethyl-3-butylimidzolium tetrafluoroborate, 1-ethyl-2,3-dimethylimidazolium tetrafluoroborate, 1-ethyl-3,5-dimethylimidazolium tetrafluoroborate, 1,3-diethyl-5-methylimidazolium tetrafluoroborate, and 1-ethylimidazolium tetrafluoroborate; an imidazolium chloride substituted with one or more alkyl groups wherein the above tetrafluoroborate anion is replaced with a chloride anion; an imidazolium bromide substituted with one or more alkyl groups wherein the above tetrafluoroborate anion is replaced with a bromide anion; an imidazolium iodide substituted with one or more alkyl groups wherein the above tetrafluoroborate anion is replaced with an iodide anion; an imidazolium hexafluorophosphate substituted with one or more alkyl groups wherein the above tetrafluoroborate anion is replaced with a tetrafluorophosphate anion; an imidazolium bis(perfluoroalkanesufonyl)amide substituted with one or more alkyl groups wherein the above tetrafluoroborate anion is replaced with a bis(perfluoroalkanesulfonyl)amide anion; an imidazolium alkylcarboxylate substituted with one or more alkyl groups wherein the above tetrafluoroborate anion is replaced with an alkylcarboxylate anion; and an imidazolium alkanesulfonate substituted with one or more alkyl groups wherein the above tetrafluoroborate anion is replaced with an alkanesulfonate anion.

Examples of the pyridinium salt substituted with one or more alkyl groups include, for example, those which are composed of a pyridinium cation, of which at least one nitrogen atom on the pyridine ring is bonded to the above-mentioned substituted or unsubstituted alkyl group, and the above-mentioned anionic species. Specific examples thereof include, for example, a pyridinium tetrafluoroborate substituted with one or more alkyl groups such as N-methylpyridinium tetrafluoroborate, N-ethylpyridinium tetrafluoroborate, N-propylpyridinium tetrafluoroborate, N-butylpyridinium tetrafluoroborate, N-butyl-4-methylpyridinium tetrafluoroborate, N-isobutylpyridinium tetrafluoroborate, and N-pentylpyridinium tetrafluoroborate; a pyridinium chloride substituted with one or more alkyl groups wherein the above tetrafluoroborate anion is replaced with a chloride anion; a pyridinium bromide substituted with one or more alkyl groups wherein the above tetrafluoroborate anion is replaced with a bromide anion; a pyridinium iodide substituted with one or more alkyl groups wherein the above tetrafluoroborate anion is replaced with an iodide anion; a pyridinium hexafluorophosphate substituted with one or more alkyl groups wherein the above tetrafluoroborate anion is replaced with a tetrafluorophosphate anion; a pyridinium bis(perfluoroalkanesufonyl)amide substituted with one or more alkyl groups wherein the above tetrafluoroborate anion is replaced with a bis(perfluoroalkanesulfonyl)amide anion; a pyridinium alkylcarboxylate substituted with one or more alkyl groups wherein the above tetrafluoroborate anion is replaced with an alkylcarboxylate anion; and a pyridinium alkanesulfonate substituted with one or more alkyl groups wherein the above tetrafluoroborate anion is replaced with an alkanesulfonate anion.

Examples of the quaternary ammonium salt include, for example, salts composed of the ammonium cations, which are composed of four the above-mentioned substituted or unsubstituted alkyl groups, which may be the same or different, and nitrogen atoms, and the above-mentioned anionic species. Examples thereof include, for example, a quaternary ammonium tetrafluoroborate such as trimethylpentylammonium tetrafluoroborate, trimethylhexylammonium tetrafluoroborate, trimethylheptylammonium tetrafluoroborate, trimethyloctylammonium tetrafluoroborate and triethylpentylammonium tetrafluoroborate; a quaternary ammonium hexafluorophosphate substituted with one or more alkyl groups wherein the above tetrafluoroborate anion is replaced with a tetrafluorophosphate anion; a quaternary ammonium bis(perfluoroalkanesufonyl)amide substituted with one or more alkyl groups wherein the above tetrafluoroborate anion is replaced with a bis(perfluoroalkanesulfonyl)amide anion; a quaternary ammonium alkylcarboxylate substituted with one or more alkyl groups wherein the above tetrafluoroborate anion is replaced with an alkylcarboxylate anion; and a quaternary ammonium alkanesulfonate substituted with one or more alkyl groups wherein the above tetrafluoroborate anion is replaced with an alkanesulfonate anion.

Examples of the quaternary phosphonium salt include, for example, salts composed of the ammonium cations which are composed of four the above-mentioned substituted or unsubstituted alkyl groups, which may be the same or different, and phosphorus atoms, and the above-mentioned anionic species. Examples thereof include, for example, a quaternary phosphonium tetrafluoroborate such as trimethylpentylphosphonium tetrafluoroborate and tetrabutylphosphonium tetrafluoroborate; a quaternary phosphonium hexafluorophosphate substituted with one or more alkyl groups wherein the above tetrafluoroborate anion is replaced with a hexafluorophosphate anion; a quaternary phosphonium bis(perfluoroalkanesufonyl)amide substituted with one or more alkyl groups wherein the above tetrafluoroborate anion is replaced with a bis(perfluoroalkanesulfonyl)amide anion; a quaternary phosphonium alkylcarboxylate substituted with one or more alkyl groups wherein the above tetrafluoroborate anion is replaced with an alkylcarboxylate anion; a quaternary phosphonium alkanesulfonate substituted with one or more alkyl groups wherein the above tetrafluoroborate anion is replaced with an alkanesulfonate anion.

Examples of the tertiary sulfonium salt include, for example, salts composed of the sulfonium cations, which are composed of three the above-mentioned substituted or unsubstituted alkyl groups, which may be the same or different, and sulfur atoms, and the above-mentioned anionic species. Examples thereof include, for example, a tertiary sulfonium tetrafluoroborate such as triethylsulfonium tetrafluoroborate, tributylsulfonium tetrafluoroborate and tripropylsulfonium tetrafluoroborate; a tertiary sulfonium hexafluorophosphate substituted with one or more alkyl groups wherein the above tetrafluoroborate anion is replaced with a hexafluorophosp hate anion; a tertiary sulfonium bis(perfluoroalkanesufonyl)amide substituted with one or more alkyl groups wherein the above tetrafluoroborate anion is replaced with a bis(perfluoroalkanesulfonyl)amide anion; a tertiary sulfonium alkylcarboxylate substituted with one or more alkyl groups wherein the above tetrafluoroborate anion is replaced with an alkylcarboxylate anion; a tertiary sulfonium alkanesulfonate substituted with one or more alkyl groups wherein the above tetrafluoroborate anion is replaced with an alkanesulfonate anion.

The amount used of the ionic liquid is not particularly limited and it is usually about 0.1 to 100 parts by weight relative to 1 part by weight of the selenium compound.

The present invention is usually carried out without using a solvent, and may be carried out in the presence of a solvent. Examples of the solvent include, for example, ether solvents such as diethyl ether, methyl tert-butyl ether and tetrahydrofuran; ester solvents such as ethyl acetate; alcohol solvents such as methanol, ethanol, and tert-butanol; nitrile solvents such as acetonitrile and propionitrile; and water. The solvent may be used alone or in the form of a mixture. The amount used of the solvent is not particularly limited.

In the present reaction, the reaction is carried out in the presence of an aromatic carboxylic acid to obtain the oxygen-containing compound in better yield. Examples of the aromatic carboxylic acid include, for example, benzoic acid, salicylic acid, 4-hydroxybenzoic acid, 3-hydroxybenzoic acid, 3,4-dihydroxybenzoic acid, 3,4,5-trihydroxybenzoic acid, picolinic acid, nicotinic acid, and isonicotinic acid. The amount used of the aromatic carboxylic acid is not limited particularly and it is practically 0.1 to 10 moles per 1 mole of the selenium compound.

In the present reaction, the olefin compound, the ionic liquid, the organic hydroperoxide, the selenium compound and if necessary the solvent and/or the aromatic carboxylic acid, may be mixed and the mixing order is not limited particularly. A preferable example of the mixing order is described below. First, the ionic liquid, the selenium compound and a part of the organic hydroperoxide are mixed. In this case, if necessary, the aromatic carboxylic acid may be mixed thereto. Next, the olefin compound is added to the mixture, and then the remaining organic hydroperoxide is added thereto and the resulting mixture is stirred at the reaction temperature to obtain the oxygen-containing compound in good yield.

If the reaction temperature is too low, the reaction hardly proceeds and, if the reaction temperature is too high, side reaction such as polymerization of the starting olefin compound may proceed. Therefore, the practical reaction temperature is in a range of 0 to 200° C.

The reaction may be carried out under a normal pressure or pressurized condition. The progress of the reaction can be checked by conventional analyzing means such as gas chromatography, high performance liquid chromatography, thin layer chromatography, NMR and IR.

After completion of the reaction, a solvent immiscible with the ionic liquid is added to the reaction mixture as it is or after decomposition of the remaining organic hydroperoxide with a reducing agent such as sodium sulfite if necessary, and the ionic liquid phase and organic phase containing an oxygen-containing compound can be separated. When the aqueous solution is used at the point of the reaction or the aftertreatment with the reducing agent, the reaction mixture is sometimes separated to the three phases of the ionic liquid phase, the organic phase containing oxygen-containing compound and the aqueous phase and in this case each phase may be also separated to obtain the organic phase containing oxygen-containing compound and the ionic liquid phase. The oxygen-containing compound can be isolated by concentrating the obtained organic phase. The isolated oxygen-containing compound may be further purified by a conventional purification means such as distillation or column chromatography.

Examples of the organic solvent immiscible with the ionic liquid include, for example, aliphatic hydrocarbon solvents such as n-pentane, n-hexane and n-heptane, and aromatic hydrocarbon solvents such as toluene and xylene and the amount used of the organic solvent is not particularly limited.

The selenium compound or the oxide of the above-mentioned selenium compound is usually contained in the above-mentioned ionic liquid phase and the ionic liquid phase containing the selenium compound or the oxide of the above-mentioned selenium compound, as it is or after conducting concentration treatment if necessary, can be used again in the present reaction. When the ionic liquid phase is used again, new selenium compound may be not used and if necessary, a selenium compound may be used by adding to the ionic liquid phase.

Examples of the alcohol compound among thus obtained oxygen-containing compounds include, for example, E,E-2,6-dimethyl-2,6-octadiene-8-acetoxy-1-ol, E,E-2,6-dimethyl-2,6-octadiene-8-benzoyloxy-1-ol, E,E-2,6-dimethyl-2,6-octadiene-8-methoxy-1-ol, E,E-2,6-dimethyl-2,6-octadien-8-benzyloxy-1-ol, E,E-2,6-dimethyl-2,6-octadien-1-ol-8-phenylsulfone, E,E-11-hydroxy-6,10-dimethyl-5,9-undecadien-2-one, E-2-methyl-4-acetate-2-butene-1,4-diol, 6-hydroxy-7-octenoic acid methyl ester, 1-hexen-3-ol, 1-hepten-3-ol, 1-octen-3-ol, 1-dodecen-3-ol, 1-hydroxy-2-cyclopentene, 2-methyl-2-cyclohexen-1-ol, 2,5-dimethyl-2-cyclohexen-1-ol, 1-hydroxy-2-cyclohexene, 1-hydroxy-2-cycloheptene, 1-hydroxy-2-cyclooctene, 1-hydroxy-4-methyl-2-cyclopentene, 1-hydroxy-5-methyl-2-cyclopentene, 1-hydroxy-4,5-dimethyl-2-cyclopentene, 1-hydroxy-4-chloro-2-cyclopentene, 1-hydroxy-4-methyl-2-cyclohexene, 4-hydroxy-2-hexene, 3-hydroxy-1,7-octadiene, 3-hydroxy-1,2,3,6-tetrahydrophthalic anhydride, 1-inden-1-ol, 3-phenyl-2-propen-1-ol, 1,3-diphenyl-2-propen-1-ol, 6-(hydroxymethyl)-4-methoxy-2H-pyran-2-one, 2-phenyl-2-propen-1-ol, 2-methylenecyclobutanol, 2-methylenecyclopentanol, pinocarveol, dihydro-4-hydroxy-3-methylene-2-furanone, 2-cyclohexylidenecyclohexanol, 2-(2-hydroxy-1-methylmethylidene)-5-methylcyclohexanone, 3-hydroxymethyl-5,5-dimethyl-2-cyclohexen-1-one, 2-caren-10-ol, isochamol and myrtenol.

Examples of the aldehyde compound include, for example, E,E-2-formyl-8-acetoxy-6-methyl-2,6-octadiene, E,E-2-formyl-8-benzoyloxy-6-methyl-2,6-octadiene, E,E-2-formyl-8-methoxy-6-methyl-2,6-octadiene, E,E-2-formyl-8-benzyloxy-6-methyl-2,6-octadiene, E,E-2-formyl-8-phenylsulfone-6-methyl-2,6-octadiene, E,E-2,6-dimethyl-10-oxo-2,6-undecadienal, E-4-(acetyloxy)-2-methyl-2-butenal, α-formylstyrene, 3-phenyl-2-propenal, 4-methoxy-2-oxo-2H-pyran-6-carboxyaldehyde, 2-(4-methyl-2-cyclohexylidene)propanal, formylisophorone, 7,7-dimethyl-2-norcarene-3-carboxyaldehyde, 7,7-dimethyl-3-norcarene-3-carboxyaldehyde and myrtenal.

Examples of the ketone compound include, for example, 6-oxo-7-octenoic acid methyl ester, 3-oxo-1-hexene, 3-oxo-1-heptene, 3-oxo-1-octene, 3-oxo-1-dodecene, 2-cyclopentenone, 2-methyl-2-cyclohexen-1-one, 2,5-dimethyl-2-cyclohexen-1-one, 2-cyclohexenone, 2-cycloheptenone, 2-cyclooctenone, 4-methyl-2-cyclopentenone, 5-methyl-2-cyclopentenone, 4,5-dimethyl-2-cyclopentenone, 4-chloro-2-cyclopentenone, 4-methyl-2-cyclohexenone, 4-oxo-2-hexene, 3-oxo-1,7-octadiene, 3-oxo-1,2,3,6-tetrahydrophthalic anhydride, inden-1-one, 1,3-diphenyl-2-propen-1-one, 2-methylenecyclobutanone, 2-methylenecyclopentanone, pinocarvone, dihydro-4-oxo-3-methylene-2-furanone, and 2-cyclohexylidenecyclohexanone.

Examples of the carboxylic acid compound include, for example, E,E-2-carboxy-8-acetoxy-6-methyl-2,6-octadiene, E,E-2-carboxy-8-benzoyloxy-6-methyl-2,6-octadiene, E,E-2-carboxy-8-methoxy-6-methyl-2,6-octadiene, E,E-2-carboxy-8-benzyloxy-6-methyl-2,6-octadiene, E,E-2-carboxy-8-phenylsulfone-6-methyl-2,6-octadiene, E,E-2,6-dimethyl-10-oxo-2,6-undecadienoic acid, E-4-(acetyloxy)-2-methyl-2-butenoic acid, α-carboxystyrene, cinnamic acid, 2-(4-methyl-2-cyclohexylidene)propanoic acid, 5,5-dimethyl-3-oxo-1-cyclohexene-1-carboxylic acid, 7,7-dimethyl-bicyclo[4.1.0]hept-2-ene-3-carboxylic acid, chaminic acid and myrtenic acid.

Next, an application of the present invention is illustrated below with a specific example, but the present invention is not limited by this example.

When a compound of formula (8)

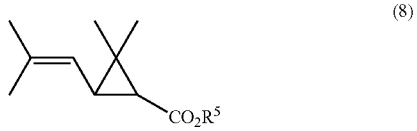

(8)

wherein $R^5$ represents a substituted or unsubstituted alkyl group, a substituted or unsubstituted aryl group, or a substituted or unsubstituted aralkyl group (hereinafter, simply referred to as the chrysanthemic acid ester (8)), for example, is used as the olefin compound in the present invention, at least one compound selected from a compound of formula (9)

(9)

wherein $R^5$ is as defined above (hereinafter, simply referred to as the alcohol (9)), a compound of formula (10)

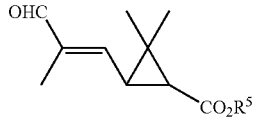

(10)

wherein $R^5$ is as defined above (hereinafter, simply referred to as the aldehyde (10)), and a compound of formula (11)

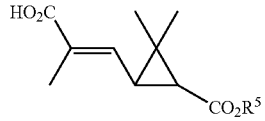

(11)

wherein $R^5$ is as defined above (hereinafter, simply referred to as the carboxylic acid (11)), can be obtained as the oxygen-containing compound.

Examples of a substituted or unsubstituted alkyl group, a substituted or unsubstituted aryl group, and a substituted or unsubstituted aralkyl group include the same as exemplified above.

Examples of the compound represented by formula (10) and (11) include preferably the compound wherein $R^5$ is i) an alkyl group, or ii) an aralkyl group which may be substituted with at least one group selected from an alkyl group, an alkoxy group, a halogen atom, an alkoxyalkyl group and an aryloxy group, more preferably the compound wherein $R^5$ is i) a methyl group or ethyl group, or ii) a benzyl group which may be substituted with at least one group selected from a methyl group, a methoxy group, a halogen atom, a methoxymethyl group and a phenoxy group.

Examples of the chrysanthemic acid ester (8) include, for example, methyl 3,3-dimethyl-2-(2-methyl-1-propenyl)cyclopropanecarboxylate, ethyl 3,3-dimethyl-2-(2-methyl-1-propenyl)cyclopropanecarboxylate, isopropyl 3,3-dimethyl-2-(2-methyl-1-propenyl)cyclopropanecarboxylate, tert-butyl 3,3-dimethyl-2-(2-methyl-1-propenyl)cyclopropanecarboxylate, cyclohexyl 3,3-dimethyl-2-(2-methyl-1-propenyl)cyclopropanecarboxylate, menthyl 3,3-dimethyl-2-(2-methyl-1-propenyl)cyclopropanecarboxylate, benzyl 3,3-dimethyl-2-(2-methyl-1-propenyl)cyclopropanecarboxylate, 4-chlorobenzyl 3,3-dimethyl-2-(2-methyl-1-propenyl)cyclopropanecarboxylate, 2,3,5,6-tetrafluorobenzyl 3,3-dimethyl-2-(2-methyl-1-propenyl)cyclopropanecarboxylate, 2,3,5,6-tetrafluoro-4-methylbenzyl 3,3-dimethyl-2-(2-methyl-1-propenyl)cyclopropanecarboxylate, 2,3,5,6-tetrafluoro-4-methoxybenzyl 3,3-dimethyl-2-(2-methyl-1-propenyl)cyclopropanecarboxylate, 2,3,5,6-tetrafluoro-4-methoxymethylbenzyl 3,3-dimethyl-2-(2-methyl-1-propenyl)cyclopropanecarboxylate, and 3-phenoxybenzyl 3,3-dimethyl-2-(2-methyl-1-propenyl)cyclopropanecarboxylate.

The chrysanthemic acid ester (8) has a cis-isomer having the group shown by —$CO_2R^5$ and the 2-methyl-1-propenyl group on the same side with respect to the cyclopropane ring plane and a trans-isomer having the groups on the opposite side, and any one of the cis-isomer and the trans-isomer or a mixture thereof may be used in the present invention.

When the mixture thereof is used, a mixing ratio of the cis-isomer and trans-isomer is not particularly limited.

The chrysanthemic acid ester (8) has asymmetric carbon atoms within the molecule. Therefore, the chrysanthemic acid ester (8) has optical isomers and any one optical isomer thereof or a mixture thereof may be used in the present invention.

Examples of the alcohol (9) among the obtained oxygen-containing compounds include, for example, methyl 3,3-dimethyl-2-E-(2-hydroxymethyl-1-propenyl)cyclopropanecarboxylate, ethyl 3,3-dimethyl-2-E-(2-hydroxymethyl-1-propenyl)cyclopropanecarboxylate, isopropyl 3,3-dimethyl-2-E-(2-hydroxymethyl-1-propenyl)cyclopropanecarboxylate, tert-butyl 3,3-dimethyl-2-E-(2-hydroxymethyl-1-propenyl)cyclopropanecarboxylate, cyclohexyl 3,3-dimethyl-2-E-(2-hydroxymethyl-1-propenyl)cyclopropanecarboxylate, menthyl 3,3-dimethyl-2-E-(2-hydroxymethyl-1-propenyl)cyclopropanecarboxylate, benzyl 3,3-dimethyl-2-E-(2-hydroxymethyl-1-propenyl)cyclopropanecarboxylate, 4-chlorobenzyl 3,3-dimethyl-2-E-(2-hydroxymethyl-1-propenyl)cyclopropanecarboxylate, 2,3,5,6-tetrafluorobenzyl 3,3-dimethyl-2-E-(2-hydroxymethyl-1-propenyl)cyclopropanecarboxylate, 2,3,5,6-tetrafluoro-4-methylbenzyl 3,3-dimethyl-2-E-(2-hydroxymethyl-1-propenyl)cyclopropanecarboxylate, 2,3,5,6-tetrafluoro-4-methoxybenzyl 3,3-dimethyl-2-E-(2-hydroxymethyl-1-propenyl)cyclopropanecarboxylate, 2,3,5,6-tetrafluoro-4-methoxymethylbenzyl 3,3-dimethyl-2-E-(2-hydroxymethyl-1-propenyl)cyclopropanecarboxylate, and 3-phenoxybenzyl 3,3-dimethyl-2-E-(2-hydroxymethyl-1-propenyl)cyclopropanecarboxylate.

Examples of the aldehyde (10) include, for example, methyl 3,3-dimethyl-2-E-(2-formyl-1-propenyl)cyclopropanecarboxylate, ethyl 3,3-dimethyl-2-E-(2-formyl-1-propenyl)cyclopropanecarboxylate, isopropyl 3,3-dimethyl-2-E-(2-formyl-1-propenyl)cyclopropanecarboxylate, tert-butyl 3,3-dimethyl-2-E-(2-formyl-1-propenyl)cyclopropanecarboxylate, cyclohexyl 3,3-dimethyl-2-E-(2-formyl-1-propenyl)cyclopropanecarboxylate, menthyl 3,3-dimethyl-2-E-(2-formyl-1-propenyl)cyclopropanecarboxylate, benzyl 3,3-dimethyl-2-E-(2-formyl-1-propenyl)cyclopropanecarboxylate, 4-chlorobenzyl 3,3-dimethyl-2-E-(2-formyl-1-propenyl)cyclopropanecarboxylate, 2,3,5,6-tetrafluorobenzyl 3,3-dimethyl-2-E-(2-formyl-1-propenyl)cyclopropanecarboxylate, 2,3,5,6-tetrafluoro-4-methylbenzyl 3,3-dimethyl-2-E-(2-formyl-1-propenyl)cyclopropanecarboxylate, 2,3,5,6-tetrafluoro-4-methoxybenzyl 3,3-dimethyl-2-E-(2-formyl-1-propenyl)cyclopropanecarboxylate, 2,3,5,6-tetrafluoro-4-methoxymethylbenzyl 3,3-dimethyl-2-E-(2-formyl-1-propenyl)cyclopropanecarboxylate, and 3-phenoxybenzyl 3,3-dimethyl-2-E-(2-formyl-1-propenyl)cyclopropanecarboxylate.

Examples of the carboxylic acid (11) include, for example, methyl 3,3-dimethyl-2-E-(2-carboxy-1-propenyl)cyclopropanecarboxylate, ethyl 3,3-dimethyl-2-E-(2-carboxy-1-propenyl)cyclopropanecarboxylate, isopropyl 3,3-dimethyl-2-E-(2-carboxy-1-propenyl)cyclopropanecarboxylate, tert-butyl 3,3-dimethyl-2-E-(2-carboxy-1-propenyl)cyclopropanecarboxylate, cyclohexyl 3,3-dimethyl-2-E-(2-carboxy-1-propenyl)cyclopropanecarboxylate, menthyl 3,3-dimethyl-2-E-(2-carboxy-1-propenyl)cyclopropanecarboxylate, benzyl 3,3-dimethyl-2-E-(2-carboxy-1-propenyl)cyclopropanecarboxylate, 4-chlorobenzyl 3,3-dimethyl-2-E-(2-carboxy-1-propenyl)cyclopropanecarboxylate, 2,3,5,6-tetrafluorobenzyl 3,3-dimethyl-2-E-(2-carboxy-1-propenyl)cyclopropanecarboxylate, 2,3,5,6-tetrafluoro-4-methylbenzyl 3,3-dimethyl-2-E-(2-carboxy-1-propenyl)cyclopropanecarboxylate, 2,3,5,6-tetrafluoro-4-methoxybenzyl 3,3-dimethyl-2-E-(2-carboxy-1-propenyl)cyclopropanecarboxylate, 2,3,5,6-tetrafluoro-4-methoxymethylbenzyl 3,3-dimethyl-2-E-(2-carboxy-1-propenyl)cyclopropanecarboxylate, and 3-phenoxybenzyl 3,3-dimethyl-2-E-(2-carboxy-1-propenyl)cyclopropanecarboxylate.

According to the reaction of the present invention, typically three compounds represented by the formula (9), (10) and (11), the compounds represented by the formula (9) and (10), or the compounds represented by the formula (10) and (11) were produced, and if necessary, each compound can be separated by distillation, column chromatography and extraction as the above.

When a trans-isomer of the chrysanthemic acid ester (8) is used, a trans-isomer of the oxygen-containing compound (which is alcohol (9) and/or aldehyde (10) and/or carboxylic acid (11)) is obtained, and when a cis-isomer of the chrysanthemic acid ester (8) is used, a cis-isomer of the oxygen-containing compound is obtained. When an optically active chrysanthemic acid ester (8) is used, an optically active oxygen-containing compound is obtained.

Thus obtained alcohol (9), aldehyde (10) and carboxylic acid (11) are important compounds as the synthetic intermediates for pyrethroid household agents for epidemic prevention and insecticides and the present reaction can be applied to the industrial method for preparing these compounds.

EXAMPLES

The present invention is illustrated below in more detail with examples, but the present invention is not limited by these examples. The yield of methyl 3,3-dimethyl-2-E-(2-hydroxymethyl-1-propenyl)cyclopropanecarboxylate and methyl 3,3-dimethyl-2-E-(2-carboxy-1-propenyl)cyclopropanecarboxylate was calculated based on the results analyzed by liquid chromatography internal standard method and the yield of the other compound was calculated based on the results analyzed by gas chromatography internal reference method.

Example 1

Into a 100 mL flask equipped with a magnetic rotor and a reflux condenser, 50 mg of selenium dioxide, 100 mg of 3,4-dihydroxybenzoic acid, 1 g of 1-butyl-3-methylimidazolium tetrafluoroborate and 1 g of 70 wt % aqueous tert-butylhydroperoxide were charged. The mixture was stirred and maintained for 30 minutes at an inner temperature of 40° C. After that, 1.5 g of methyl 3,3-dimethyl-2-(2-methyl-1-propenyl)cyclopropanecarboxylate was added to the mixture, and the resulting mixture was heated to an inner temperature of 60° C. To the mixture, 1.64 g of 70 wt % aqueous tert-butylhydroperoxide was added dropwise over 1 hour at the same temperature and the resulting mixture was stirred to effect the reaction for 5 hours at the same temperature. After completion of the reaction, the reaction mixture was cooled to room temperature. 10 g of n-hexane was added to the reaction mixture and the extracting treatment was carried out to obtain a n-hexane phase and an ionic liquid phase. The ionic liquid phase was extracted two times by n-hexane and obtained n-hexane phase was mixed to the n-hexane phase obtained before to obtain an organic phase containing oxygen-containing compounds.

1.5 g of an ionic liquid phase containing 1-butyl-3-methylimidazolium tetrafluoroborate was obtained.

Yield of Each Component

Methyl 3,3-dimethyl-2-E-(2-hydroxymethyl-1-propenyl)cyclopropanecarboxylate: 3%, Methyl 3,3-dimethyl-2-E-(2-formyl-1-propenyl)cyclopropanecarboxylate: 44%, Methyl 3,3-dimethyl-2-E-(2-carboxy-1-propenyl)cyclopropanecarboxylate: 42%.

Example 2

After 1.5 g of the ionic liquid phase obtained in example 1 and 1.5 g of methyl 3,3-dimethyl-2-(2-methyl-1-propenyl)cyclopropanecarboxylate were charged into a 100 mL flask equipped with a magnetic rotor and a reflux condenser, the resulting mixture was heated to an inner temperature of 60° C. and 2.6 g of 70 wt % aqueous tert-butylhydroperoxide was added dropwise over 1 hour at the same temperature with stirring, and then the mixture was heated to an inner temperature of 80° C. and stirred to effect the reaction for 3 hours at the same temperature. After completion of the reaction, the reaction mixture was cooled to room temperature. 10 g of n-hexane was added to the reaction mixture and the extracting treatment was carried out to obtain a n-hexane phase and an ionic liquid phase. The ionic liquid phase was extracted two times by n-hexane and obtained n-hexane phase was mixed to the n-hexane phase obtained before to obtain an organic phase containing oxygen-containing compounds. 1.6 g of an ionic liquid phase containing 1-butyl-3-methylimidazolium tetrafluoroborate was obtained.

Yield of Each Component

Methyl 3,3-dimethyl-2-E-(2-hydroxymethyl-1-propenyl)cyclopropanecarboxylate: 7%, Methyl 3,3-dimethyl-2-E-(2-formyl-1-propenyl)cyclopropanecarboxylate: 43%, Methyl 3,3-dimethyl-2-E-(2-carboxy-1-propenyl)cyclopropanecarboxylate: 33%.

Example 3

Into a 100 mL flask equipped with a magnetic rotor and a reflux condenser, 50 mg of selenium dioxide, 100 mg of picoline, 1 g of 1-butyl-3-methylimidazolium tetrafluoroborate and 0.5 g of 70 wt % aqueous tert-butylhydroperoxide were charged. The mixture was stirred and maintained for 30 minutes at an inner temperature of 40° C. After that, 1.5 g of methyl 3,3-dimethyl-2-(2-methyl-1-propenyl)cyclopropanecarboxylate was added to the mixture, and the resulting mixture was heated to an inner temperature of 60° C. To the mixture, 2.2 g of 70 wt % aqueous tert-butylhydroperoxide was added dropwise over 1 hour at the same temperature with stirring. The resulting mixture was heated to an inner temperature of 80° C. and stirred to effect the reaction for 2 hours at the same temperature. After completion of the reaction, the reaction mixture was cooled to room temperature. 10 g of n-hexane was added to the reaction mixture and the extracting treatment was carried out to obtain a n-hexane phase and an ionic liquid phase. The ionic liquid phase was extracted two times by n-hexane and obtained n-hexane phase was mixed to the n-hexane phase obtained before to obtain an organic phase containing oxygen-containing compounds. 1.5 g of an ionic liquid phase containing 1-butyl-3-methylimidazolium tetrafluoroborate was obtained.

Yield of Each Component 3,3-dimethyl-2-E-(2-hydroxymethyl-1-propenyl)cyclopropanecarboxylate: 8%, Methyl 3,3-dimethyl-2-E-(2-formyl-1-propenyl)cyclopropanecarboxylate: 54%, Methyl 3,3-dimethyl-2-E-(2-carboxy-1-propenyl)cyclopropanecarboxylate: 8%.

Example 4

Into a 100 mL flask equipped with a magnetic rotor and a reflux condenser, 1.5 g of the ionic liquid phase obtained in example 3 and 1.5 g of methyl 3,3-dimethyl-2-(2-methyl-1-propenyl)cyclopropanecarboxylate were charged and the resulting mixture was heated to an inner temperature of 60° C. After 2.6 g of 70 wt % aqueous tert-butylhydroperoxide was added dropwise over 1 hour to the mixture at the same temperature with stirring, the resulting mixture was stirred to effect the reaction for 5 hours at the same temperature. After completion of the reaction, the reaction mixture was cooled to room temperature. 10 g of n-hexane was added to the reaction mixture and the extracting treatment was carried out to obtain a n-hexane phase and an ionic liquid phase. The ionic liquid phase was extracted two times by n-hexane and obtained n-hexane phase was mixed to the n-hexane phase obtained before to obtain an organic phase containing oxygen-containing compounds. 1.6 g of an ionic liquid phase containing 1-butyl-3-methylimidazolium tetrafluoroborate was obtained.

Yield of Each Component

Methyl 3,3-dimethyl-2-E-(2-hydroxymethyl-1-propenyl)cyclopropanecarboxylate: 36%, Methyl 3,3-dimethyl-2-E-(2-formyl-1-propenyl)cyclopropanecarboxylate: 37%, Methyl 3,3-dimethyl-2-E-(2-carboxy-1-propenyl)cyclopropanecarboxylate: 7%.

Example 5

Into a 100 mL flask equipped with a magnetic rotor and a reflux condenser, 50 mg of selenium dioxide, 1 g of 1-butyl-3-methylimidazolium tetrafluoroborate and 0.5 g of 70 wt % aqueous tert-butylhydroperoxide were charged and the mixture was stirred and maintained for 30 minutes at an inner temperature of 40° C. After that, 1.5 g of methyl 3,3-dimethyl-2-(2-methyl-1-propenyl)cyclopropanecarboxylate was added to the mixture, and the resulting mixture was heated to an inner temperature of 70° C. To the mixture, 2.2 g of 70 wt % aqueous tert-butylhydroperoxide was added dropwise over 1 hour at the same temperature with stirring.

The resulting mixture was stirred to effect the reaction for 7 hours at the same temperature. After completion of the reaction, the reaction mixture was cooled to room temperature. 10 g of n-hexane was added to the reaction mixture and the extracting treatment was carried out to obtain a n-hexane phase and an ionic liquid phase. The ionic liquid phase was extracted two times by n-hexane and obtained n-hexane phase was mixed to the n-hexane phase obtained before to obtain an organic phase containing oxygen-containing compounds. 1.4 g of an ionic liquid phase containing 1-butyl-3-methylimidazolium tetrafluoroborate was obtained.

Yield of Each Component

Methyl 3,3-dimethyl-2-E-(2-hydroxymethyl-1-propenyl)cyclopropanecarboxylate: 20%, Methyl 3,3-dimethyl-2-E-(2-formyl-1-propenyl)cyclopropanecarboxylate: 44%, Methyl 3,3-dimethyl-2-E-(2-carboxy-1-propenyl)cyclopropanecarboxylate: 16%.

Example 6

Into a 100 mL flask equipped with a magnetic rotor and a reflux condenser, 1.4 g of the ionic liquid phase obtained in example 5 and 1.5 g of methyl 3,3-dimethyl-2-(2-methyl-1-propenyl)cyclopropanecarboxylate were charged and the resulting mixture was heated to an inner temperature of 70° C. After 2.6 g of 70 wt % aqueous tert-butylhydroperoxide was added dropwise over 1 hour to the mixture at the same temperature with stirring, the resulting mixture was stirred to effect the reaction for 6 hours at the same temperature. After completion of the reaction, the reaction mixture was cooled to room temperature. 10 g of n-hexane was added to the reaction mixture and the extracting treatment was carried out to obtain a n-hexane phase and an ionic liquid phase. The ionic liquid phase was extracted two times by n-hexane and obtained n-hexane phase was mixed to the n-hexane phase obtained before to obtain an organic phase containing oxygen-containing compounds. 1.6 g of an ionic liquid phase containing 1-butyl-3-methylimidazolium tetrafluoroborate was obtained.

Yield of Each Component

Methyl 3,3-dimethyl-2-E-(2-hydroxymethyl-1-propenyl)cyclopropanecarboxylate: 34%, Methyl 3,3-dimethyl-2-E-(2-formyl-1-propenyl)cyclopropanecarboxylate: 21%, Methyl 3,3-dimethyl-2-E-(2-carboxy-1-propenyl)cyclopropanecarboxylate: 5%, 35% of the starting methyl 3,3-dimethyl-2-(2-methyl-1-propenyl)cyclopropanecarboxylate was remained.

Example 7

Into a 100 mL flask equipped with a magnetic rotor and a reflux condenser, 50 mg of selenium dioxide, 100 mg of 3,4-dihydroxybenzoic acid, 1 g of 1-butyl-3-methylimidazolium tetrafluoroborate and 0.5 g of 70 wt % aqueous tert-butylhydroperoxide were charged and the mixture was stirred and maintained for 30 minutes at an inner temperature of 40° C. After that, 1.58 g of geranyl acetate was added to the mixture, and the resulting mixture was heated to an inner temperature of 50° C. To the mixture, 2.2 g of 70 wt % aqueous tert-butylhydroperoxide was added dropwise over 1 hour at the same temperature with stirring. The resulting mixture was stirred to effect the reaction for 5 hours at the same temperature. After completion of the reaction, the reaction mixture was cooled to room temperature. 10 g of n-hexane was added to the reaction mixture and the extracting treatment was carried out to obtain a n-hexane phase and an ionic liquid phase. The ionic liquid phase was extracted two times by n-hexane and obtained n-hexane phase was mixed to the n-hexane phase obtained before to obtain an organic phase containing oxygen-containing compounds. 1.5 g of an ionic liquid phase containing 1-butyl-3-methylimidazolium tetrafluoroborate was obtained.

Yield of Each Component

E,E-2,6-dimethyl-2,6-octadiene-1,8-diol-8-acetate: 35%,

E,E-2-formyl-8-acetoxy-6-methyl-2,6-octadiene: 25%, 33% of the starting geranyl acetate was remained.

Example 8

Into a 100 mL flask equipped with a magnetic rotor and a reflux condenser, 60 mg of seleninyl chloride, 1 g of 1-butyl-3-methylimidazolium tetrafluoroborate and 0.5 g of 70 wt % aqueous tert-butylhydroperoxide were charged and the mixture was stirred and maintained for 30 minutes at an inner temperature of 40° C. After that, 1.5 g of methyl 3,3-dimethyl-2-(2-methyl-1-propenyl)cyclopropanecarboxylate was added to the mixture, and the resulting mixture was heated to an inner temperature of 60° C. To the mixture, 2.2 g of 70 wt % aqueous tert-butylhydroperoxide was added dropwise over 1 hour at the same temperature with stirring. The resulting mixture was heated to an inner temperature of 80° C. and stirred to effect the reaction for 2 hours at the same temperature. After completion of the reaction, the reaction mixture was cooled to room temperature. 10 g of n-hexane was added to the reaction mixture and the extracting treatment was carried out to obtain a n-hexane phase and an ionic liquid phase. The ionic liquid phase was extracted two times by n-hexane and obtained n-hexane phase was mixed to the n-hexane phase obtained before to obtain an organic phase containing oxygen-containing compounds. 1.4 g of an ionic liquid phase containing 1-butyl-3-methylimidazolium tetrafluoroborate was obtained.

Yield of Each Component

Methyl 3,3-dimethyl-2-E-(2-hydroxymethyl-1-propenyl)cyclopropanecarboxylate: 3%, Methyl 3,3-dimethyl-2-E-(2-formyl-1-propenyl)cyclopropanecarboxylate: 32%, Methyl 3,3-dimethyl-2-E-(2-carboxy-1-propenyl)cyclopropanecarboxylate: 8%.

Example 9

Into a 100 mL flask equipped with a magnetic rotor and a reflux condenser, 1.4 g of the ionic liquid phase obtained in example 8 and 1.5 g of methyl 3,3-dimethyl-2-(2-methyl-1-propenyl)cyclopropanecarboxylate were charged and the resulting mixture was heated to an inner temperature of 60° C. 2.6 g of 70 wt % aqueous tert-butylhydroperoxide was added dropwise over 1 hour to the mixture at the same temperature with stirring. After the resulting mixture was heated to 80° C., the mixture was stirred to effect the reaction for 2 hours at the same temperature. After completion of the reaction, the reaction mixture was cooled to room temperature. 10 g of n-hexane was added to the reaction mixture and the extracting treatment was carried out to obtain a n-hexane phase and an ionic liquid phase. The ionic liquid phase was extracted two times by n-hexane and obtained n-hexane phase was mixed to the n-hexane phase obtained before to obtain an organic phase containing oxygen-containing compounds. 1.6 g of an ionic liquid phase containing 1-butyl-3-methylimidazolium tetrafluoroborate was obtained.

Yield of Each Component

Methyl 3,3-dimethyl-2-E-(2-hydroxymethyl-1-propenyl)cyclopropanecarboxylate: 22%, Methyl 3,3-dimethyl-2-E-(2-formyl-1-propenyl)cyclopropanecarboxylate: 44%, Methyl 3,3-dimethyl-2-E-(2-carboxy-1-propenyl)cyclopropanecarboxylate: 7%.

Example 10

Into a 100 mL flask equipped with a magnetic rotor and a reflux condenser, 50 mg of selenium dioxide, 1 g of N-butyl-4-methylpyridinium tetrafluoroborate and 0.5 g of 70 wt % aqueous tert-butylhydroperoxide were charged and the mixture was stirred and maintained for 30 minutes at an inner temperature of 40° C. After that, 1.5 g of methyl 3,3-dimethyl-2-(2-methyl-1-propenyl)cyclopropanecarboxylate was added to the mixture, and the resulting mixture was heated to an inner temperature of 60° C. To the mixture, 2.2 g of 70 wt % aqueous tert-butylhydroperoxide was added dropwise over 1 hour at the same temperature with stirring. After the resulting mixture was heated to an inner temperature of 80° C., the mixture was stirred to effect the reaction for 2 hours at the same temperature. After completion of the reaction, the reaction mixture was cooled to room temperature. 10 g of n-hexane was added to the reaction mixture and the extracting treatment was carried out to obtain a n-hexane phase and an ionic liquid phase. The ionic liquid phase was extracted two times by n-hexane and obtained n-hexane phase was mixed to the n-hexane phase obtained before to obtain an organic phase containing oxygen-containing compounds. 1.5 g of an ionic liquid phase containing N-butyl-4-methylpyridinium tetrafluoroborate was obtained.

Yield of Each Component

Methyl 3,3-dimethyl-2-E-(2-hydroxymethyl-1-propenyl)cyclopropanecarboxylate: 6%, Methyl 3,3-dimethyl-2-E-(2-formyl-1-propenyl)cyclopropanecarboxylate 35%, Methyl 3,3-dimethyl-2-E-(2-carboxy-1-propenyl)cyclopropanecarboxylate: 11%.

Example 11

Into a 100 mL flask equipped with a magnetic rotor and a reflux condenser, 1.5 g of the ionic liquid phase obtained in example 10 and 1.5 g of methyl 3,3-dimethyl-2-(2-methyl-1-propenyl)cyclopropanecarboxylate were charged and the resulting mixture was heated to an inner temperature of 60° C. 2.6 g of 70 wt % aqueous tert-butylhydroperoxide was added dropwise over 1 hour to the mixture at the same temperature with stirring. After the resulting mixture was heated to 80° C., the mixture was stirred to effect the reaction for 2 hours at the same temperature. After completion of the reaction, the reaction mixture was cooled to room temperature. 10 g of n-hexane was added to the reaction mixture and the extracting treatment was carried out to obtain a n-hexane phase and an ionic liquid phase. The ionic liquid phase was extracted two times by n-hexane and obtained n-hexane phase was mixed to the n-hexane phase obtained before to obtain an organic phase containing oxygen-containing compounds. 1.6 g of an ionic liquid phase containing N-butyl-4-methylpyridinium tetrafluoroborate was obtained.

Yield of Each Component

Methyl 3,3-dimethyl-2-E-(2-hydroxymethyl-1-propenyl)cyclopropanecarboxylate: 24%, Methyl 3,3-dimethyl-2-E-(2-formyl-1-propenyl)cyclopropanecarboxylate: 35%, Methyl 3,3-dimethyl-2-E-(2-carboxy-1-propenyl)cyclopropanecarboxylate: 8%, 6% of the starting methyl 3,3-dimethyl-2-(2-methyl-1-propenyl)cyclopropanecarboxylate was remained.

Example 12

Into a 100 mL flask equipped with a magnetic rotor and a reflux condenser, 80 mg of selenocystine, 1 g of 1-ethyl-3-methylimidazolium bis(trifluoromethanesufonyl)amide, 40 mg of 98% sulfuric acid and 0.5 g of 70 wt % aqueous tert-butylhydroperoxide were charged and the mixture was stirred and maintained for 30 minutes at an inner temperature of 40° C. After that, 1.5 g of methyl 3,3-dimethyl-2-(2-methyl-1-propenyl)cyclopropanecarboxylate was added to the mixture, and the resulting mixture was heated to an inner temperature of 60° C. To the mixture, 2.2 g of 70 wt % aqueous tert-butylhydroperoxide was added dropwise over 1 hour at the same temperature with stirring. After the resulting mixture was heated to an inner temperature of 80° C., the mixture was stirred to effect the reaction for 2 hours at the same temperature. After completion of the reaction, the reaction mixture was cooled to room temperature. 10 g of n-hexane was added to the reaction mixture and the extracting treatment was carried out to obtain a n-hexane phase and an ionic liquid phase. The ionic liquid phase was extracted two times by n-hexane and obtained n-hexane phase was mixed to the n-hexane phase obtained before to obtain an organic phase containing oxygen-containing compounds. 1.4 g of an ionic liquid phase containing 1-ethyl-3-methylimidazolium bis(trifluoromethanesulfonyl)amide was obtained.

Yield of Each Component

Methyl 3,3-dimethyl-2-E-(2-hydroxymethyl-1-propenyl)cyclopropanecarboxylate: 26%, Methyl 3,3-dimethyl-2-E-(2-formyl-1-propenyl)cyclopropanecarboxylate: 39%, Methyl 3,3-dimethyl-2-E-(2-carboxy-1-propenyl)cyclopropanecarboxylate: 7%, 20% of the starting methyl 3,3-dimethyl-2-(2-methyl-1-propenyl)cyclopropanecarboxylate was remained.

Example 13

Into a 100 mL flask equipped with a magnetic rotor and a reflux condenser, 70 mg of dimethylselenourea, 1 g of 1-butyl-3-methylimidazolium tetrafluoroborate and 0.5 g of 70 wt % aqueous tert-butylhydroperoxide were charged and the mixture was stirred and maintained for 30 minutes at an inner temperature of 40° C. After that, 1.5 g of methyl 3,3-dimethyl-2-(2-methyl-1-propenyl)cyclopropanecarboxylate was added to the mixture, and the resulting mixture was heated to an inner temperature of 60° C. To the mixture, 2.2 g of 70 wt % aqueous tert-butylhydroperoxide was added dropwise over 1 hour at the same temperature with stirring. After the resulting mixture was heated to an inner temperature of 80° C., the mixture was stirred to effect the reaction for 2 hours at the same temperature. After completion of the reaction, the reaction mixture was cooled to room temperature. 10 g of n-hexane was added to the reaction mixture and the extracting treatment was carried out to obtain a n-hexane phase and an ionic liquid phase. The ionic liquid phase was extracted two times by n-hexane and obtained n-hexane phase was mixed to the n-hexane phase obtained before to obtain an organic phase containing oxygen-containing compounds. 1.4 g of an ionic liquid phase containing 1-butyl-3-methylimidazolium tetrafluoroborate was obtained.

Yield of Each Component

Methyl 3,3-dimethyl-2-E-(2-hydroxymethyl-1-propenyl)cyclopropanecarboxylate: 12%, Methyl 3,3-dimethyl-2-E-(2-formyl-1-propenyl)cyclopropanecarboxylate: 44%, Methyl 3,3-dimethyl-2-E-(2-carboxy-1-propenyl)cyclopropanecarboxylate: 8%.

The invention claimed is:

1. A method for producing an oxygen-containing compound, characterized in that an olefin compound having a carbon-carbon double bond which is bonded to a methyl or methylene group is reacted with an organic hydroperoxide in the presence of an ionic liquid and a selenium compound.

2. The method for producing an oxygen-containing compound according to claim 1, wherein the oxygen-containing compound is at least one compound selected from alcohol compounds, aldehyde compounds, ketone compounds and carboxylic acid compounds.

3. The method for producing an oxygen-containing compound according to claim 1, wherein the olefin compound having a carbon-carbon double bond which is bonded to a methyl or methylene group is a compound of formula (1)

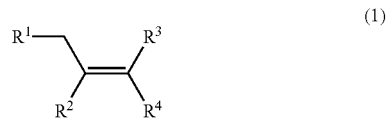

(1)

wherein $R^1$ represents a substituted or unsubstituted alkyl group, a substituted or unsubstituted aryl group, or a substituted or unsubstituted aralkyl group; $R^2$, $R^3$ and $R^4$ are the same or different, and independently represent a substituted or unsubstituted alkyl group, a substituted or unsubstituted alkoxy group, a substituted or unsubstituted aryl group, a substituted or unsubstituted aryloxy group, a substituted or unsubstituted aralkyl group, a substituted or unsubstituted aralkyloxy group, a substituted or unsubstituted alkylcarbonyl group, a substituted or unsubstituted arylcarbonyl group, a substituted or unsubstituted aralkylcarbonyl group, a substituted or unsubstituted alkoxycarbonyl group, a substituted or unsubstituted aryloxycarbonyl group, a substituted or unsubstituted aralkyloxycarbonyl group, a carboxyl group, a halogen atom or a hydrogen atom, and herein, at least one pair selected from $R^1$ and $R^3$, $R^2$ and $R^4$, $R^1$ and $R^2$, and $R^3$ and $R^4$ may be bonded together with the carbon atom to which they are bonded to form a ring, and the oxygen-containing compound is a compound of formula (2)

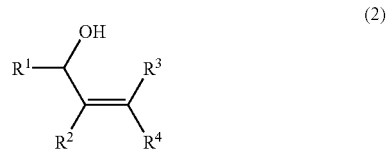

(2)

wherein $R^1$, $R^2$, $R^3$ and $R^4$ are as defined above, a compound of formula (3)

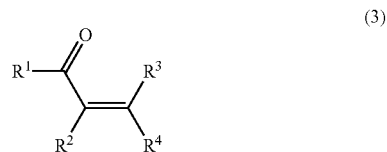

(3)

wherein $R^1$, $R^2$, $R^3$ and $R^4$ are as defined above, or a mixture thereof.

4. The method for producing an oxygen-containing compound according to claim 1, wherein the olefin compound having carbon-carbon double bond which is bonded to a methyl or methylene group is a compound of formula (4)

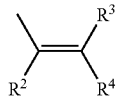
(4)

wherein $R^2$, $R^3$ and $R^4$ are as defined above, and herein, $R^2$ and $R^4$ or $R^3$ and $R^4$ may be bonded together with the carbon atom to which they are bonded to form a ring, and the oxygen-containing compound is at least one compound selected from a compound of formula (5)

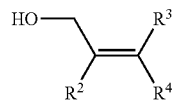
(5)

wherein $R^2$, $R^3$ and $R^4$ are as defined above, a compound of formula (6)

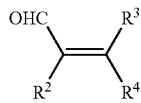
(6)

wherein $R^2$, $R^3$ and $R^4$ are as defined above, and a compound of formula (7)

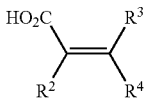
(7)

wherein $R^2$, $R^3$ and $R^4$ are as defined above.

5. The method for producing an oxygen-containing compound according to claim 1, wherein the olefin compound having carbon-carbon double bond which is bonded to a methyl or methylene group is a compound of formula (8)

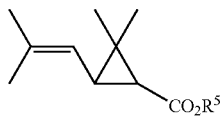
(8)

wherein $R^5$ represents a substituted or unsubstituted alkyl group, a substituted or unsubstituted aryl group, or a substituted or unsubstituted aralkyl group, and the oxygen-containing compound is at least one compound selected from a compound of formula (9)

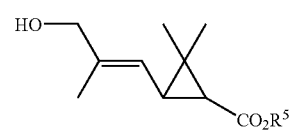
(9)

wherein $R^5$ is as defined above, a compound of formula (10)

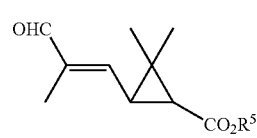
(10)

wherein $R^5$ is as defined above, and a compound of formula (11)

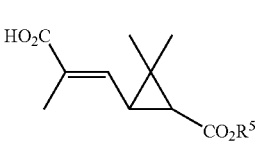
(11)

wherein $R^5$ is as defined above.

6. The method for producing according to claim 5, wherein $R^5$ is i) an alkyl group, or ii) an aralkyl group which may be substituted with at least one group selected from an alkyl group, an alkoxy group, a halogen atom, an alkoxyalkyl group and an aryloxy group.

7. The method for producing according to claim 5, wherein $R^5$ is i) a methyl group or ethyl group, or ii) a benzyl group which may be substituted with at least one group selected from a methyl group, a methoxy group, a halogen atom, a methoxymethyl group and a phenoxy group.

8. The method for producing an oxygen-containing compound according to claim 1, wherein the ionic liquid is at least one compound selected from an imidazolium salt substituted with one or more alkyl groups, a pyridinium salt substituted with one or more alkyl groups and a quaternary ammonium salt, which has a melting point of 100° C. or less and is stable to hold liquid state until high temperature of about 300° C.

9. The method for producing an oxygen-containing compound according to claim 1, wherein the selenium compound is at least one compound selected from selenium dioxide, selenic acid and selenious acid.

10. The method for producing an oxygen-containing compound according to claim 1, wherein the reaction is carried out in the presence of an aromatic carboxylic acid.

11. The method for according to claim 1, which comprises recovering the ionic liquid phase containing the selenium compound after producing an oxygen-containing compound and reusing the recovered ionic liquid phase containing the selenium compound.

12. A composition comprising at least one ionic liquid selected from an imidazolium salt substituted with one or more alkyl groups, a pyridinium salt substituted with one or more alkyl groups, and a quaternary ammonium salt, which has a melting point 100° C. or less and is stable to hold liquid state until high temperature of about 300° C., and at least one selenium compound selected from selenium dioxide, selenic acid and selenious acid, or the oxide thereof.

* * * * *